United States Patent [19]

Wei et al.

[11] Patent Number: 4,567,267
[45] Date of Patent: Jan. 28, 1986

[54] α-PHENYL-2-(AZA)BENZOTHIAZOLYLTHI-OGLYCOLIC ACIDS AND DERIVATIVES THEREOF

[75] Inventors: Peter H. L. Wei, Springfield; Francis J. Gregory, Berwyn, both of Pa.

[73] Assignee: American Home Products Corporation, New York, N.Y.

[21] Appl. No.: 413,275

[22] Filed: Aug. 30, 1982

Related U.S. Application Data

[63] Continuation-in-part of Ser. No. 273,826, Jun. 15, 1981, abandoned, which is a continuation-in-part of Ser. No. 130,483, Mar. 31, 1980, Pat. No. 4,275,065, which is a continuation-in-part of Ser. No. 50,847, Jun. 21, 1979, abandoned.

[51] Int. Cl.⁴ .................. C07D 513/04; C07D 417/12; C07D 277/74
[52] U.S. Cl. .................................... 546/114; 546/198; 548/170; 548/171
[58] Field of Search ................ 546/198, 114; 424/267, 424/256, 270; 548/170, 171; 514/301, 321, 367

[56] References Cited

U.S. PATENT DOCUMENTS 4,294,839 10/1981 Doll et al. ........................ 548/170 X

OTHER PUBLICATIONS

Potts, K., et al., *J. Org. Chem.*, 43(13), 2697–2700, (1978).

*Primary Examiner*—Richard A. Schwartz
*Attorney, Agent, or Firm*—George Tarnowski

[57] ABSTRACT

Novel α-phenyl-2-(aza)benzothiazolylthioglycolic acids, derivatives thereof and pharmacologically acceptable salts thereof are disclosed, as well as their use as intermediates in the preparation of 2-substituted-3-hydroxy-thiazolo[2,3-b]-benzothiazolium salts, 2-substituted-thiazolo[2,3-b]benzothiazol-3(2H)-one mesoionic didehydro derivatives, 2-substituted-thiazolo[2',3'-2,3]thiazolo[5,4-b]pyridin-3(2H)-one mesoionic didehydro derivatives and related compounds, and their use as modulators of the immune response.

24 Claims, No Drawings

α-PHENYL-2-(AZA)BENZOTHIAZOLYLTHIO-GLYCOLIC ACIDS AND DERIVATIVES THEREOF

This is a continuation-in-part of U.S. Ser. No. 273,826 filed June 15, 1981 now abandoned, which is a continuation in part of U.S. Ser. No. 130,483 filed Mar. 31, 1980 now U.S. Pat. No. 4,275,065 which is a continuation-in-part of U.S. Ser. No. 050,847 filed June 21, 1979, and now abandoned.

BACKGROUND OF THE INVENTION

The invention relates to novel α-phenyl-(aza)benzothiazolylthioglycolic acids, derivatives thereof and pharmacologically acceptable salts thereof, their use as intermediates in the preparation of 2-substituted-3-hydroxythiazolo[2,3-b]benzothiazolium salts, 2-substituted-thiazolo[2,3-b]-benzothiazol-3(2H)-one mesoionic didehydro derivatives, 2-substituted thiazolo[2',3'-2,3]thiazolo[5,4-b]pyridin-3(2H)-one mesoionic didehydro derivatives and related compounds, and to their use as modulators of the immune response.

In recent years, the rapid upsurge in immunological research has brought about a greater appreciation and understanding of the complexities of the immune response. While the traditional overall view of the immune system remains, new discoveries have radically changed some thinking about the details of the system. Thus, the immune system is still divided into humoral immunity, populated with B cells and responsible for antibody formation, and cell-mediated immunity, populated with T cells and responsible for the rejection of organ transplants or skin grafts, as well as the defense mechanism against various foreign biological matter and endogenous neoplastic growths.

It is only in the last decade or so, however, that the concept has been accepted that different cell populations interact in the induction and expression of both humoral and cell-mediated immunity. Thus, subpopulations of B cells and T cells have been described, such as for example "suppressor" and "helper" T cells. In a number of animal models, it has been postulated that the helper T cells act in the induction of a complete antibody response to many antigens, whereas T suppressor cells are capable of preventing or terminating such responses. It is now believed that positive and negative cellular interactions control the ultimate degree of immune response. So, it is believed that any given immune response is regulated, and that the degree and mode of regulation may ultimately explain the various reactions, diseases, and disorders which are the manifestations of the operation of the organism's immune system.

The T cell subpopulations of suppressor and helper T cells have been implicated in a number of immune response manifestations. Thus, the loss of suppressor T cells is now believed to be a major factor in such autoimmune connective tissue disease as systemic lupus erythematosus. Moreover, in the latter case, as well as in probable impaired immune system responses such as rheumatoid arthritis, it is believed the helper T cells exacerbate the condition.

Also, the theory has been advanced that T suppressor cell hypofunctioning, resulting in inadequate T-B cell cooperation in the immune response, with continuous B cell stimulation and subsequent antibody production may be the cause of the production of antigen-antibody complexes which are the causative agents of renal and inflammatory processes in arthritis and autoimmune diseases.

Thus, it is now apparent that a number of lymphopoietic disorders are undoubtedly associated with abnormalities of T cell and especially suppressor cell function. The loss of suppressor function is at least an early event in certain immune response diseases and is a disease-perpetuating mechanism in others. The loss of suppressor function probably leads to excessive lymphoid cell proliferation and may significantly contribute to lymphoproliferative disorders. The conditions created thereby may be exacerbated by helper T cells.

The role of immunomodulatory agents in the treatment of immune diseases and disorders, as well as in the attempt to prolong the life of organ transplants and skin grafts, has been to suppress the immune response, especially of cell-mediated immunity. By suppressing the cell-mediated immune response, it is possible to delay and possibly prevent the host organism from rejecting a skin graft or organ transplant, or the graft from immunologically rejecting the host (graft vs. host reaction). Similarly, enhancing or reinstituting suppressor function by immunomodulator therapy is a beneficial course of treatment for autoimmune and probable autoimmune diseases and disorders. Immunotherapy is also being recognized as an important aspect of the treatment, especially chemotherapeutic, of various forms of cancer and metastatic diseases.

The compounds of the present invention are intermediates for the preparation of highly selective immunomodulatory agents which are especially indicated in the treatment of various skin graft and organ transplant reactions, neoplastic and metastatic diseases, and immune system diseases and disorders such as systemic lupus erythematosus and rheumatoid arthritis, whose etiology is probably suppressor T cell dysfunction, and further are themselves immunomodulatory agents.

DETAILED DESCRIPTION OF THE INVENTION

The invention is directed to novel compounds having the general formula:

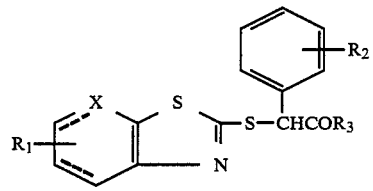

wherein $R_1$ is hydrogen, halo, nitro, amino, lower alkyl, lower alkoxy, trifluoromethyl or hydroxy; $R_2$ is hydrogen, fluorine, chlorine, bromine, lower alkyl, lower alkoxy, amino, nitro or trifluoromethyl; $R_3$ is hydroxy, lower alkoxy, amino, (lower)alkylamino, hydroxy(lower)alkyl amino, N-(lower)alkanoylamino(lower)alkoxy, N-arylcarbamoyl(lower)alkylthio, N,N-di(lower)alkylamino-N'-(lower)alkylamino, (lower)alkyl-N-(lower)alkanylamino, cyano(lower)alkylamino, prolino, cysteino or piperidino(lower)alkyl amino; X is CH or N, and where the dotted lines represent optional double bonds in the 5,6 and 7,8 positions or a pharmacologically acceptable salt thereof.

The term "lower alkyl" when used herein includes straight and branched chain hydrocarbon radicals having from 1 to about 6 carbon atoms. The terms "lower alkoxy" and "lower alkanoyl" in like manner designate radicals in which the hydrocarbon portion has 1 to about 6 carbon atoms.

The terms "halo" and "halide" when used herein refer to radicals of the elements fluorine, chlorine and bromine respectively.

The compounds of the invention are intermediates in the preparation of compounds having the formula:

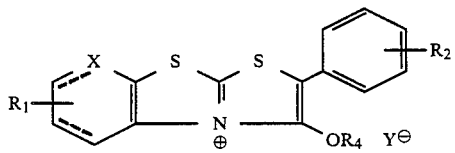

wherein $R_1$ is hydrogen, halo, amino, lower alkyl, lower alkoxy, trifluoromethyl or hydroxy; $R_2$ is fluorine, chlorine, bromine, lower alkyl, lower alkoxy, amino, nitro or trifluoromethyl; $R_4$ is hydrogen or lower alkanoyl; X is CH or N; and Y is $CF_3CO_2^-$ or a halide, and where the dotted lines represent optional double bonds in the 5,6 and 7,8 positions, which compounds are disclosed and claimed in U.S. Pat. No. 4,275,065.

These compounds can be prepared from the intermediates of the present invention according to the following reaction sequence:

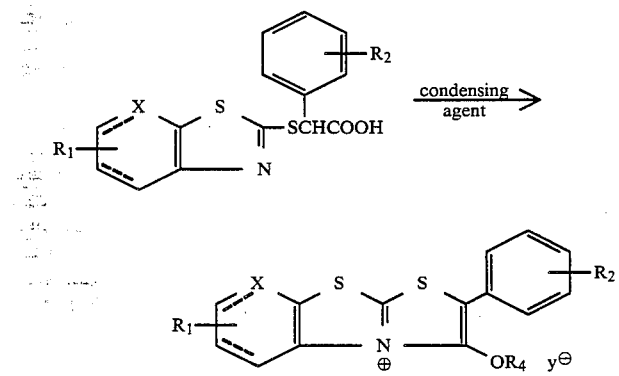

wherein $R_1$, $R_2$, X, Y and the dotted lines are as defined hereinbefore and $R_4$ may be hydrogen or the residue of the condensing agent. The reactants, in an organic solvent, such as for example acetone, and the condensing agent, such as for example, a mixture of acetic acid and acetic anhydride, trifluoroacetic anhydride and the like are heated until the solvent volume is reduced and a precipitate deposited. The precipitated solid is recrystallized to yield the desired 2-substituted-3-hydroxythiazolo[2,3-b]benzothiazolium salts or 2-substituted-3-hydroxythiazolo[2,3-b]azabenzothiazolium salts.

In the case where $R_4$ is the residue of the condensing agent and where it is desired to obtain the compound in which $R_4$ is hydrogen, the condensing agent residue can be readily removed by conventional means, as for example deacylation by heating in certain solvents. Also, in those instances in which $R_1$ is amino or hydroxy, the latter groups can be protected from acylation during the cyclization reaction by use of conventional protecting groups, for example tosyl, benzyloxycarbonyl, tert-butyl-oxycarbonyl and the like for the amino group, and acetyl, benzoyl, tert-butyl, benzyl and the like for the hydroxy group. The protecting groups can be readily removed by conventional techniques after cyclization is complete.

The benzothiazolium salts can also be transformed into their mesoionic didehydro derivatives:

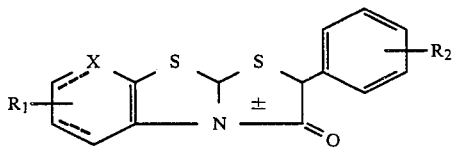

The transformation can be carried out by dissolving the benzothiazolium or azabenzothiazolium salts in a methylene chloride/water mixture, separating the organic and aqueous layers and concentrating the organic (methylene chloride) layer to recover the mesoionic didehydro derivative, which can then be further purified by recrystallization.

The intermediates of the invention can be readily prepared according to the following reaction sequence:

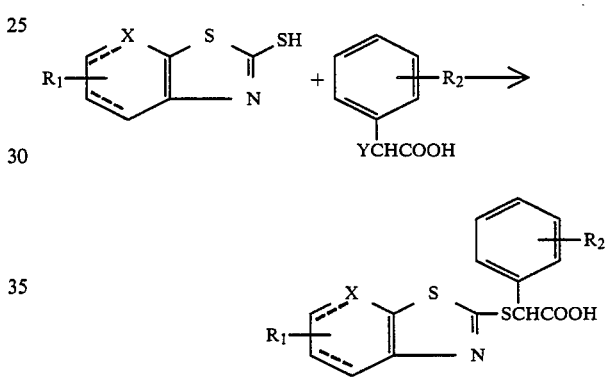

wherein $R_1$, $R_2$, X, Y and the dotted lines are as defined hereinbefore. The reaction of the appropriately substituted 2-mercapto(aza)benzothiazole and the α-halophenylacetic acid is carried out in an organic solvent, such as for example acetone and can be performed at room temperature or at elevated temperatures. The substituted-2-mercapto(aza)benzothiazoles can be reacted in their alkali metal or alkaline earth metal salt form. The reaction can also be carried out in the presence of a scavenging agent for the liberated hydrohalide, such as a tertiary amine, for example triethylamine. This is preferred in the preparation of the azabenzothiazolylthioglycolic acids.

The derivatives of the intermediate α-phenyl-2-(aza)-benzothiazolylthioglycolic acids of the invention are most conveniently prepared by reacting the tricyclic mesoionic didehydro compounds described supra with appropriate nucleophilic reactants. This reaction, involving the ring cleavage of the terminal thiazole ring, is as follows:

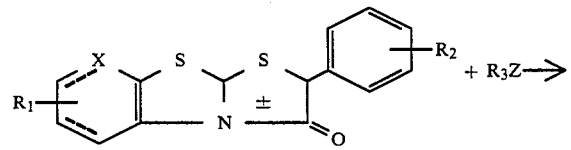

-continued

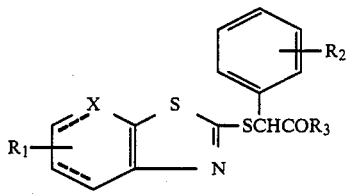

wherein R₁, R₂, R₃, and X are as described hereinbefore and R₃Z is a nucleophilic reactant bearing the desired R₃ substituent. This reaction provides compounds of the invention which are otherwise inaccessible by conventional means. The reaction is carried out in a suitable organic solvent, such as for example methylene chloride and over a range of temperatures, such as room temperature as well as under reflux conditions, depending on the nature of the nucleophilic reactant being used.

In addition to their use as intermediates, the compounds of the invention are themselves immunomodulators. The compounds have therapeutic application in a variety of situations in which immunomodulation is indicated. Thus, the compounds are useful in treating allograft reactions, organ transplant reactions, and graft vs. host reactions. The compounds permit the host to accept the graft without destroying the host's immunity to other infections. The compounds are also useful in the treatment of autoimmune diseases, such as systemic lupus erythematosus (SLE). Further, the compounds of the invention inhibit the production of the immunoglobulins, which are so pathologic to autoimmune disease such as SLE, as well as the production of antigen-antibody complexes which are the causative agents of renal and inflammatory processes in arthritis and autoimmune diseases. Thus, the compounds of the invention are also useful in the treatment of such conditions as rheumatoid arthritis. Moreover, the compounds can be used in the treatment of neoplastic diseases, as well as metastatic diseases.

Accordingly, the invention is further directed to a method of modulating the immune response in warm-blooded animals in need of modulation of the immune response by administering to a warm-blooded animal an amount effective to bring about said modulation of the immune response of a compound having the general formula:

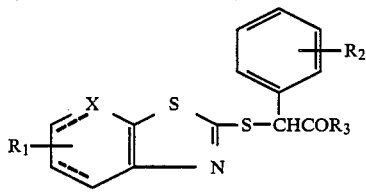

wherein R₁ is hydrogen, halo, amino, lower alkyl, lower alkoxy, trifluoromethyl or hydroxy; R₂ is hydrogen, fluorine, chlorine, bromine, lower alkyl, lower alkoxy, amino, nitro or trifluoromethyl; R₃ is hydroxy, lower alkoxy, amino, (lower)alkylamino, hydroxy(lower)alkylamino, N-(lower)alkanoylamino(lower)alkoxy, N-arylcarbamoyl(lower)alkylthio, N,N-di(lower)alkylamino-N'-(lower)alkanoylamino, (lower)alkyl-N-(lower)alkanoylamino, cyano(lower)alkylamino, prolino, cysteino or piperidino(lower)alkylamino; X is CH or N; and where the dotted lines represent optional double bonds in the 5,6 and 7,8 positions, or a pharmacologically acceptable salt thereof.

When the compounds of the invention are employed as immunomodulators, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The compounds may be encapsulated with or without other carriers. In all cases the proportion of active ingredients in said compositions both solid and liquid will be at least sufficient to impart immunomodulatory activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration level that will generally afford effective results without causing any harmful or deleterious side effects. With large animals (about 70 kg. body weight), for injection administration the dose is from about 25 milligrams to about 50 milligrams and for oral administration the dose is from about 50 milligrams to about 200 milligrams and preferably from about 50 milligrams to about 100 milligrams per day either as a single unit dose, or if desired, the dosage may be divided into convenient subunits administered at convenient times throughout the day.

The immunomodulatory effect of the compounds of the invention may be demonstrated by standard pharmacological and histological procedures. The pharmacological procedures are described more fully in the examples given hereinafter.

These procedures illustrate the ability of the compounds of the invention to exert an immunomodulatory effect, especially selectively on the cell-mediated immunity by directly measuring the effect of the compounds on the humoral and cell-mediated immunity, and include evaluation of the compounds in the Plescia anti-SRBC antibody production assay, evaluation in the mitogen activated murine T lymphocyte proliferation test and evaluation of the compounds against the metastatic spread of murine Lewis lung carcinoma.

EXAMPLE 1

α-(2-Benzothiazolylthio)benzeneacetic acid

A. α-(2-Benzothiazolylthio)benzene acetic acid, hydrobromide

A solution of 16.7 g (0.10 m) 2-mercaptobenzothiazole and 21.5 g (0.10 m) α-bromo-α-phenylacetic acid in acetone is heated to reflux for 5 hours and the solvent is then removed. The residual oil is triturated in acetone and 31 g of solid collected. The compound melts at 192°–4° C.

Analysis for: $C_{15}H_{11}NO_2S_2 \cdot HBr$: Calculated: C, 47.12; H, 3.17; N, 3.66; Br, 20.90; S, 16.77. Found: C, 47.22; H, 3.06; N, 3.69; Br, 20.93; S, 16.73.

B. α-(2-Benzothiazolylthio)benzene acetic acid

The hydrobromide salt of A above is stirred in water at room temperature overnight, the solid collected and air dried. The crude material is recrystallized from acetonitrile to give the title compound in 70% yield and melting at 152°–4° C.

Analysis for: $C_{15}H_{11}NO_2S_2$: Calculated: C, 59.78; H, 3.68; N, 4.65. Found: C, 59.81; H, 3.85; N, 4.77.

EXAMPLE 2

α-(5-Chlorobenzothiazol-2-ylthio)-benzene acetic acid 50.0 g (0.248 m) 5-chloro-2-mercaptobenzothiazole and 53.0 g (0.248 m) α-bromophenylacetic acid are dissolved in 1.5 l acetone and the solution is heated for 4 hours in the presence of 50 ml glacial acetic acid. The solution is concentrated to a smaller volume (about 200 ml) and the residual solid (90 g) is collected. The resulting salt is suspended in 1 l of water and the mixture is stirred at room temperature overnight. The collected solid is recrystallized from 2.5 l acetonitrile to give a total of 64 g (85% yield) of title compound melting at 190°–2° C.

Analysis for: $C_{15}H_{10}ClNO_2S_2$: Calculated: C, 53.64; H, 3.00; N, 4.17. Found: C, 53.83; H, 3.13; N, 4.13.

EXAMPLE 3

Sodium salt of α-(5-chlorobenzothiazol-2-ylthio)benzene acetic acid

To a solution of 10 g (0.03 m) of the compound of Example 2 in 600 ml of acetone is added an alcoholic NaOH (1.2 g (0.03 m) in 20 ml ethanol) solution. The precipitate is collected and recrystallized from water. 8.0 g (71% yield) of title compound is isolated as a monohydrate melting at 238°–42° C. (dec.).

Analysis for: $C_{15}H_9ClNO_2S_2Na H_2O$: Calculated: C, 47.93; H, 2.95; N, 3.73. Found: C, 47.7; H, 3.12; N, 3.79.

EXAMPLE 4

α-(5-chlorobenzothiazol-2-ylthio)-α-(p-chlorophenyl)acetic acid

Method A

An acetone solution of 12.1 g (0.06 m) 5-chloro-2-mercaptobenzothiazole and 15.0 g (0.06 m) α-bromo-α-(p-chlorophenyl)-acetic acid is heated in the presence of 30 ml glacial acetic acid for 5 hours. After solvent removal, the residual solid is collected. This solid (9 g of the hydrobromide salt of the title compound) is stirred in water overnight and the solid is collected and air dried. The crude material is recrystallized from acetonitrile to give 4.7 g (21% yield) of the title compound melting at 157°–8° C.

Method B

An acetone solution of the potassium salt of 5-chloro-2-mercaptobenzothiazole (0.05 m) and α-bromo-α-(p-chlorophenyl)-acetic acid (0.05 m) are heated to reflux for 3 days. The solid (KBr), formed during the reaction, is filtered off and the filtrate is concentrated, and the residual solid triturated with a mixture of acetone and hexane. The crude material is recrystallized from benzene to give 7.7 g (42% yield) of title compound melting at 157°–8° C.

Method C

A methylene chloride solution of 10.0 g (0.05 m) 5-chloro-2-mercaptobenzothiazole, 12.5 g (0.05 m) α-bromo-α-(p-chlorophenyl)-acetic acid and 10.0 g (0.10 m) triethylamine is heated to reflux overnight. The reaction mixture is washed first with a dilute hydrochloric acid solution, then with water and finally dried over $MgSO_4$. After the methylene chloride is removed, the residual solid is triturated with acetonitrile to give 13.6 g (74% yield) of title compound melting at 157°–8° C.

Analysis for: $C_{15}H_9Cl_2NO_2S_2$: Calculated: C, 48.65; H, 2.45; N, 3.78. Found: C, 48.69; H, 2.58; N, 3.79.

EXAMPLE 5

α-(p-Chlorophenyl)-α-(benzothiazol-2-yl-thio)acetic acid

Following the procedure of Example 4, Method C and substituting 2-mercaptobenzothiazole for 5-chloro-2-mercaptobenzothiazole, the title compound is prepared in 34% yield and having a melting point of 185°–7° C. (dec.).

Analysis for: $C_{15}H_{10}ClNO_2S_2$: Calculated: C, 53.64; H, 3.00; N, 4.17. Found: C, 54.07; H, 3.17; N, 4.13.

EXAMPLE 6

Preparation of 6-Chloro-2-phenylthiazolo[2,3-b]benzothiazol-3(2H)-one mesoionic didehydro derivative 31 g (0.092 m) of the compound of Example 2 is suspended in 3.5 l methylene chloride and the mixture is heated to gentle reflux in the presence of 25 ml acetic anhydride. The solid is gradually dissolved, the solution turning reddish. After heating overnight, the solution is filtered and concentrated to 200 ml. The residual orange solid, weighing 29.5 g (quantitative yield), is collected and has a melting point of 215°–6° C.

EXAMPLE 7

α-(5-Chlorobenzothiazol-2-ylthio)benzene acetic acid 7 g of the compound of Example 6 is dissolved in 100 ml N,N-dimethylacetamide and the solution is allowed to stand at room temperature for 2 days in the presence of 5 ml water. The solution is diluted with 120 ml water and the resulting solid is collected and air dried. The crude material is recrystallized from 500 ml benzene. 5.9 g (80% yield) of purified title compound is obtained, having a melting point of 190°–1° C.

Analysis for: $C_{15}H_{10}ClNO_2S_2$: Calculated: C, 53.64; H, 3.00; N, 4.17. Found: C, 53.83; H, 3.13; N, 4.13.

EXAMPLE 8

α-(5-Chloro-2-benzothiazolylthio)benzene acetic acid, ethyl ester 8.0 g of the compound of Example 6 is dissolved in ethanol and the solution is warmed over a steam bath until the orange color is discharged. The solvent is removed and oily residue is recrystallized from hexane. 6.6 g (73% yield) of title compound is obtained, having a melting point of 62°–4° C.

Analysis for: $C_{17}H_{14}ClNO_2S_2$: Calculated: C, 56.11; H, 3.88; N, 3.85. Found: C, 56.05; H, 3.92; N, 3.84.

EXAMPLE 9

α-(5-Chlorobenzothiazol-2-ylthio)-αphenylacetamide

To 6.0 g (0.189 m) of the compound of Example 6 in 300 ml methylene chloride is introduced gaseous ammonia. The orange solid dissolves with discharge of the orange coloration followed by the precipitation of a white solid. After 15 minutes, the introduction of ammonia is stopped and the mixture is stirred for 30 minutes. The solid is collected and a further quantity of solid is recovered upon removal of the solvent from the filtrate. The combined solids are recrystallized from acetonitrile to give 5.0 g (79% yield) of title compound having a melting point of 181°–3° C.

Analysis for: $C_{15}H_{11}ClN_2OS_2$: Calculated: C, 53.80; H, 3.31; N, 8.37. Found: C, 53.67; H, 3.41; N, 8.44.

EXAMPLE 10

α-[(5-Chloro-2-benzothiazolyl)thio]-N-(2-hydroxyethyl)benzene acetamide 6.2 g (0.02 m) of the compound of Example 6 and 1.2 g (0.02 m) ethanolamine in a methylene chloride solution are warmed over a steam bath until dissolution is complete and the coloration discharged. The solution is filtered and the solvent removed. The residue is triturated with ether, the solid is collected and dried in a drying oven. 6.2 g (82% yield) of title compound, having a melting point of 148°–9° C., is obtained.

Analysis for: $C_{17}H_{15}ClN_2O_2S_2$: Calculated: C, 53.88; H, 3.99; N, 7.40. Found: C, 54.03; H, 4.14; N, 7.46.

EXAMPLE 11

α-[(5-Chloro-2-benzothiazolyl)thio]benzene acetic acid, [2-(acetylamino)ethyl]ester 3.18 g (0.01 m) of the compound of Example 6 and 1.03 g (0.01 m) N-acetylethanolamine are dissolved in methylene chloride and the solution is heated to reflux for 3 days. After removal of the solvent, the oily residue is recrystallized from 100 ml ether. 3.5 g (83% yield) of title compound, having a melting point of 107°–8° C., is obtained.

Analysis for: $C_{19}H_{17}ClN_2O_3S_2$: Calculated: C, 54.21; H, 4.07; N, 6.66. Found: C, 53.95; H, 4.14; N, 6.59.

EXAMPLE 12

α-[(5-Chloro-2-benzothiazolyl)thio]benzeneethanethioic acid, S-[2-(2-naphthalenylamino)-2-oxoethyl]ester 3.18 g (0.01 m) of the compound of Example 6 and 2.17 g (0.01 m) α-mercapto-N-(2-naphthyl)acetamide are dissolved in methylene chloride and the mixture is heated to reflux for 7 days. The progress of the reaction is monitored by TLC. After removal of solvent, the residue is recrystallized from ether. 2.3 g (42% yield) of title compound, having a melting point of 144°–5° C., is obtained.

Analysis for: $C_{27}H_{19}ClN_2O_2S_3$: Calculated: C, 60.60; H, 3.58; N, 5.24. Found: C, 60.89; H, 3.78; N, 5.27.

EXAMPLE 13

α-[(5-Chlorothiazolo[5,4-b]pyridin-2-yl)thio]α-phenyl acetic acid

A methylene chloride solution of 4.05 g (0.02 m) 5-chloro-2-mercaptothiazolo[5,4-b]pyridine, 4.30 g (0.02 m) α-bromophenylacetic acid and 4.0 g (0.04 m) triethylamine is heated to gentle reflux overnight. The methylene chloride solution is extracted twice with a dilute hydrochloric acid solution and once with water and then dried over anhydrous MgSO₄. After the solvent is removed, the residual solid is recrystallized from acetonitrile. 5.0 g (74% yield) of title compound, melting at 175°–7° C., is obtained.

Analysis for: $C_{14}H_9ClN_2O_2S_2$: Calculated: C, 49.92; H, 2.69; N, 8.32. Found: C, 49.97; H, 2.85; N, 8.37.

EXAMPLE 14

α-[(5-Chlorothiazolo[5,4-b]pyridin-2-yl)thio]-α-(p-chlorophenyl)acetic acid

A methylene chloride solution of 6.0 g (0.03 m) of 5-chloro-2-mercaptothiazolo[5,4-b]pyridine, 7.5 g (0.03 m) α-bromo-α-(p-chlorophenyl)acetic acid and 6.0 g (0.06 m) triethylamine is heated to gentle reflux overnight. The solution is extracted twice with a dilute hydrochloric acid solution and then once with water. After drying over anhydrous MgSO₄, the solvent is removed and the residual solid is recrystallized from acetonitrile. 7.5 g (68% yield) of title compound, melting at 144°–6° C., is obtained.

Analysis for: $C_{14}H_8Cl_2N_2O_2S_2$: Calculated: C, 45.29; H, 2.17; N, 7.55. Found: C, 44.87; H, 2.27; N, 7.59.

EXAMPLE 15

α-Phenyl-α-[(4,5,6,7-tetrahydrobenzothiazol-2-yl)thio]acetic acid

A methylene chloride solution of 5.13 g (0.03 m) 2-mercapto-4,5,6,7-tetrahydrobenzothiazole, 6.45 g. (0.03 m) α-bromophenylacetic acid and 6.0 g (0.06 m) triethylamine is heated to gentle reflux overnight. The solution is extracted twice with a dilute hydrochloric acid solution, once with water and is then dried over anhydrous MgSO₄. The residual solid after solvent removal is recrystallized from acetonitrile. 7.0 g (77% yield) of title compound, melting at 118°–20° C., is obtained Analysis for: $C_{15}H_{15}NO_2S_2$: Calculated: C, 58.99; N, 4.95; N, 4.59. Found: C, 59.0; H, 4.94; N, 4.52.

EXAMPLE 16

α-[(6-Nitro-2-benzothiazolyl)thio]benzeneacetic acid

A methylene chloride solution of 5.0 g (0.0235 m) 2-mercapto-6-nitrobenzothiazole, 5.2 g (0.0235 m) α-bromophenylacetic acid and 5.0 g (0.05 m) triethylamine is heated to gentle reflux overnight. The solution is washed twice with a dilute hydrochloric acid solution and once with water. The solution is dried over anhydrous MgSO₄ and then concentrated. The residue is recrystallized once from benzene and then from acetonitrile. 1.5 g (18% yield) of title compound, having a melting point of 152°–5° C., is obtained.

Analysis for: $C_{15}H_{10}N_2O_4S_2$: Calculated: C, 52.01; H, 2.91; N, 8.09. Found: C, 51.72; H, 2.97; N, 8.01.

EXAMPLE 17

α-[(5-Chloro-2-benzothiazolyl)thio]-N-methyl-benzeneacetamide 2.8 g (0.088 m) of the compound of Example 6 is suspended in 300 ml methylene chloride and the mixture is warmed over a steam bath. Gaseous monomethylamine is gradually bubbled into the mixture. The orange coloration is discharged immediately followed by complete dissolution of the solid. After 10 minutes the solvent is removed, the solid triturated with ether and the solid is collected. The crude material is recrystallized from 80 ml of acetonitrile, to give 2.3 g (77% yield) of the title compound, which has a melting point of 170°–1° C.

Analysis for: $C_{16}H_{13}ClN_2OS_2$: Calculated: C, 55.08; H, 3.75; N, 8.03. Found: C, 55.02; H, 3.86; N, 8.2.

EXAMPLE 18

α-[(5-chloro-2-benzothiazolyl)thio]-N-[2-(dimethylamino)ethyl]benzeneacetamide

Following the procedure of Example 17, and substituting unsym dimethylethylenediamine for monomethylamine, there is obtained a 92% yield of the title compound having a melting point of 108°–9° C.

Analysis for: $C_{19}H_{20}ClN_3OS_2$: Calculated: C, 56.21; H, 4.97; N, 10.35. Found: C, 55.78; H, 4.89; N, 10.19.

EXAMPLE 19

4-Chloro-α-(5-Chloro-2-benzothiazolyl)thio]benzeneacetamide

Following the procedure of Example 17, and substituting gaseous ammonia for monomethylamine, there is obtained a 74% yield of the title compound having a melting point of 204°–5° C.

Analysis for: $C_{15}H_{11}ClN_2OS_2$: Calculated: C, 48.78; H, 2.73; N, 7.59. Found: C, 48.46; H, 2.77; N. 7.59.

EXAMPLE 20

N-[[(5-Chloro-2-benzothiazolyl)thio]-phenylacetyl]glycine, ethyl ester

A. N-(α-Chlorophenylacetyl)glycine, ethyl ester 21.0 g (0.11 m) α-chlorophenylacetyl chloride and 14.0 g (0.10 m) glycine ethyl ester hydrochloride are suspended in 500 ml toluene and the mixture is heated to reflux overnight. The reaction mixture is filtered, and after the solvent is removed, the residual solid is recrystallized from cyclohexane to give 22 g (86% yield) of the title compound, which has a melting point of 88°–9° C.

Analysis for: $C_{12}H_{14}ClNO_3$: Calculated: C, 56.36; H, 5.52; N, 5.48. Found: C, 56.15; H, 5.47; N, 5.46.

B.
N-[[(5-Chloro-2-benzothiazolyl)thio]phenylacetyl]glycine, ethyl ester 5.11 g (0.02 m) of the compound prepared in A above, 4.0 g (0.02 m) 5-chloro-2-mercaptobromothiazole and 2.0 g (0.02 m) triethylamine are dissolved in methylene chloride and the mixture is heated overnight. The reaction mixture is washed with water and then dried over anhydrous magnesium sulfate. After removal of solvent, the residual solid is recrystallized from benzene to give 3.3 g (39% yield) of the title compound, which has a melting point of 132°–4° C.

Analysis for: $C_{19}H_{17}ClN_2O_3S_2$: Calculated: C, 54.21; H, 4.07; N, 6.66. Found: C, 54.17; H, 4.11; N, 6.76.

EXAMPLE 21

α-[(5-Chloro-2-benzothiazolyl)thio]-N-(cyanomethyl)benzeneacetamide

A. α-Chloro-N-(cyanomethyl)benzeneacetamide 9.2 g (0.10 m) aminoacetonitrile and 19.0 g (0.11 m) α-chlorophenylacetyl chloride are heated to reflux in methylene chloride for 4 hours. The reaction mixture is filtered and the solvent is removed. The residual solid is recrystallized from benzene to give 16.7 g (80% yield) of the title compound, which has a melting point of 73°–4° C.

Analysis for: $C_{10}H_9ClN_2O$: Calculated: C, 57.56; H, 4.35; N, 13.43. Found: C, 57.55; H, 4.37; N, 13.26.

B.
α-[(5-Chloro-2-benzothiazolyl)thio]-N-(cyanomethyl)benzeneacetamide

By following the procedure of Example 20B, and substituting α-chloro-N-(cyanomethyl)benzeneacetamide for N-(α-chlorophenylacetyl)glycine, ethyl ester, there is obtained a 39% yield of the title compound, which has a melting point of 167°–9° C.

Analysis for: $C_{17}H_{12}ClN_3OS_2$: Calculated: C, 54.61; H, 3.25; N, 11.24. Found: C, 54.49; H, 3.36; N, 11.13.

EXAMPLE 22

1-[[(2-benzothiazolyl)thio]phenylacetyl]-L-proline 5.7 g (0.02 m) 2-phenylthiazolo[2,3-b]benzothiazol-3(2H)-one mesoionic didehydro derivative, 2.2 g (0.02 m)-L-(-)-proline and 2.0 g (0.02 m) triethylamine are suspended in methylene chloride and the mixture is stirred at room temperature overnight. The reaction mixture is extracted with a dilute hydrochloric acid solution and dried over anhydrous magnesium sulfate. After the solvent is removed, the residue is extracted with hot cyclohexane. The solid obtained from the cyclohexane solution is recrystallized from acetonitrile. In order to remove all traces of acetonitrile, the solid is ground, stirred in water for 3 days, collected and then dried in an oven at 90° C. There is thereby obtained 3.0 g (37% yield) of the title compound, which has a melting point of 174°–5° C. (dec).

Analysis for: $C_{20}H_{18}N_2O_3S_2$: Calculated: C, 60.28; H, 4.55; N, 7.03. Found: C, 60.13; H, 4.48; N, 7.15.

EXAMPLE 23

1-[[(5-Chloro-2-benzothiazolyl)thio]phenylacetyl]-L-proline 11.0 g (0.0346 m) of the compound of Example 6, 4.0 g (0.0348 m) L-(-)-proline and 7.0 g (0.07 m) triethylamine are heated to reflux in methylene chloride for 4 hours. The reaction mixture is washed with a dilute hydrochloric acid solution and dried over anhydrous magnesium sulfate. After solvent removal, the residual solid is triturated with hexane and collected. The crude material is recrystallized from acetonitrile to give 9.0 g (60% yield) of the title compound, which has a melting point of 160°–1° C.

Analysis for: $C_{20}H_{17}ClN_2O_3S_2$: Calculated: C, 55.49; H, 3.96; N, 6.47. Found: C, 55.35; H, 3.94; N, 6.45.

EXAMPLE 24

α-[(5-Chloro-2-benzothiazolyl)thio]-N-[2-(1)-piperidinyl)ethyl]benzeneacetamide

Following the procedure of Example 17, and substituting 2-piperidinoethylamine for monomethylamine, there is obtained a 9.7% yield of the title compound, which has a melting point of 108°–9° C.

Analysis for: $C_{22}H_{24}ClN_3OS_2$: Calculated: C, 59.24; H, 5.42; N, 9.42. Found: C, 59.26; H, 5.49; N, 9.5.

EXAMPLE 25

N-[[(5-Chloro-2-benzothiazolyl)thio]phenylacetyl]-L-cysteine 6.36 g (0.02 m) of the compound of Example 6, 2.4 g (0.02 m) L-(-)-cysteine and 2.5 g (0.025 m) triethylamine are suspended in methylene chloride (800 ml) and the mixture is heated for 56 hours. After filtering off some insoluble material, the filtrate is washed with a dilute hydrochloric acid solution and then dried over anhydrous magnesium sulfate. The oily residue left after solvent removal is triturated with ether and the solid is collected. The ether solution, upon standing, yields more solid. The combined solids are recrystallized from acetonitrile to give 1.5 g (17% yield) of the title compound, which has a melting point of 155°–8° C.

Analysis for: $C_{18}H_{15}ClN_2O_3S_3$: Calculated: C, 49.25; H, 3.44; N, 6.38. Found: C, 49.36; H, 3.45; N, 6.0.

EXAMPLE 26

The Plescia anti-SRBC (sheep red blood cells) antibody induction assay is a very sensitive test which is used to measure the ability of an immunomodulatory agent to augment or depress SRBC-induced production of SRBC-specific IgM and IgG antibodies. That is, this assay provides specific information regarding the ability of an immunomodulatory agent to induce the entire immune system to provide an enhanced or depressed antibody response to challenge with an antigen, which in the assay is SRBC. The effect of potential immunomodulatory compounds on T cells and their various subpopulations, as well as on B cells, can be studied in this assay.

The total assay procedure is essentially in three parts. In the first part, antigen-primed splenocytes (spleen cells) are prepared. C57B1/6J male mice are injected intraperitoneally with $10^7$ SRBC (in pyrogen-free isotonic saline). Ten days later, the animals are sacrificed, their spleens excised and a suspension of spleen cells is prepared therefrom. The suspension is prepared using 1 ml of tissue culture medium (Click medium supplemented with 10% fetal calf serum) per spleen and all suspensions are pooled into a single suspension. The number of viable nucleated spleen cells in the suspension is counted and adjusted to $10^7$/ml.

In the second part, 1 ml of the above suspension of primed spleen cells is added to sterile culture tubes to which is added 1 ml of a standard suspension of SRBC ($10^7$/ml of tissue culture medium). Stock solutions of compounds to be tested are prepared in tissue culture medium and from this appropriate dilutions are made to cover a range of concentrations. To each culture tube is added 0.1 ml of each compound dilution, while 0.1 ml of medium alone is added to the control tubes. The tubes are capped, mixed and then placed in a humidified-5% $CO_2$ incubator at 37° C. for 6 days. The tubes are then centrifuged at 1000 xg for about 10 minutes to sediment the cells and the supernatants decanted into test tubes.

In the third part, 2-fold serial dilutions of the supernatants, from 1/1 to 1/32, are made and 0.1 ml of each dilution is added to individual test tubes. To each tube there is added 0.1 ml of SRBC ($10^9$/ml), the tubes are mixed and allowed to stand at room temperature for 15–30 minutes. Then 0.1 ml complement (guinea pig serum diluted to contain a slight excess of complement) is added to each tube, mixed and the tubes are placed in a 37° C. water bath for lysis of SRBC to occur. Only SRBC that have been sensitized by anti-SRBC antibody in the supernatant will lyse. 2.0 ml of isotonic saline is added to each tube, mixed and centrifuged to sediment unlysed cells and to recover the supernatant containing hemoglobin from the lysed SRBC. The supernatants' absorbance is measured at 541 nn.

Since the percent of SRBC that is lysed is proportional to the amount of anti-SRBC antibody present in the test cell culture supernatant, and since lysis is measured in terms of the hemoglobin that is released from the lysed SRBC, it is the absorbance of the released hemoglobin that is measured in order to determine the quantity of anti-SRBC antibody present in the supernatant. Because the assay is most precise at the range of 50% lysis of SRBC in the presence of excess complement, the volume of supernatant that produces 50% lysis of SRBC, by definition, contains 1 unit of antibody called a 50% hemolytic unit (H50). One divided by this volume gives the number of H50's per ml of test supernatant. A standard curve of absorbance vs. H50/ml for control supernatant is then prepared, and the concentration of antibody in other test culture supernatants, for each dilution, is determined. The content of anti-SRBC antibody for the various test compounds at their various concentrations shows whether the compound has caused stimulation or suppression of the immune response.

The results of this assay for several compounds of the invention are tabulated in Table 1, where the data is presented as H50 units of anitbody/ml and % change from control.

TABLE 1

| Compound (of Example No) | Quantity µg/ml | Units of Antibody | % Change from Control |
|---|---|---|---|
| | Experiment 1 | | |
| Example 2 | 25 | 30.32 | −428 |
| | 2.5 | 84.96 | −147 |
| Example 4 | 25 | 62.3 | −200 |
| | 2.5 | 124.6 | 0 |
| Control | — | 124.9 | — |
| | Experiment 2 | | |
| Example 4 | 25 | 47.53 | −348 |
| Example 3 | 25 | 48.26 | −343 |
| Control | — | 165.4 | — |

The results show that the compounds of the invention have a profound and significant depressive effect on the immune response, an effect which is further substantiated by the results in the mitogen activated murine T lymphocyte proliferation test.

EXAMPLE 27

An in vivo modification of the in vitro Plescia assay of Example 26 is carried out to test other compounds of the invention.

In the modified assay, the testing is carried out in vivo. Accordingly, the mice are sensitized on day 0 with the intraperitoneal injection of SRBC. One day 1, the animals are dosed with the test compounds and 5–6 days thereafter, the animals are bled. The collected blood samples are centrifuged to obtain blood serum as the supernatant. The supernatant is then treated as in part three of the procedure described in Example 26. The results of this testing are tabulated in Table 2.

TABLE 2

| Compound of Example No. | Dosage mg/kg | Units of Antibody | % Change from Control |
|---|---|---|---|
| | Experiment 1 | | |

TABLE 2-continued

| Compound of Example No. | Dosage mg/kg | Units of Antibody | % Change from Control |
|---|---|---|---|
| Example 21 | 25 | 6.32 | −395 |
| Control | 1 ml saline/mouse | 24.46 | — |
| Experiment 2 | | | |
| Example 18 | 25 | 159.6 | −141 |
| Control | 1 ml saline/mouse | 225.1 | — |

The results confirm the activity found for other compounds of the invention as already described in Example 26, supra.

EXAMPLE 28

The mitogen activated murine T lymphocyte proliferation test is used to determine the effects of immunomodulatory agents on the proliferation of murine T cell populations. The test is run to determine whether test compounds will enhance or depress the proliferation of T cells, whose proliferation has been initially stimulated by a mitogen, such as Concanavallin A (Con A). To exclude the possibility that the test compounds act at Con A binding sites, the T cell proliferation can be studied in a system in which the test compounds are incubated with the T cells prior to the addition Con A instead of in a system in which test compounds and Con A are added to the cell cultures concomitantly.

The test procedure is as follows:

T lymphocytes are isolated from spleens of male CBA/J or NZB mice. Cell homogenates are prepared in Hank's balanced salt solution (HBSS). After removal of larger particles and repeated washing of the cells in HBSS they are suspended in minimum essential medium (MEM) and passed through a glass wool column to remove macrophages. The cells are then incubated on a nylon wool column at 37° C., 95% air, 5% $CO_2$, for 45 minutes. The non-adherant T lymphocytes are then eluted from the column, counted, and adjusted to $20 \times 10^6$ cells/ml. 50 μl of cells are cultured (37° C., 95% air, 5% $CO_2$) with compound, or compound and mitogen (0.025 μg/culture of Concanavalin A) for 48 hours before the addition of 0.5 μCi of $^3$H-thymidine for the last 16 hours of culture. The total volume of the culture system is 200 μl. The cells are then harvested on a multiple automatic sample harvester (Mash II), the glass fiber filter disks placed in 10 ml of xylene base scintillation fluid, and counted for 1 minute in a liquid scintillation counter.

The incubation experiments are conducted in two ways:

(1) lymphocytes are incubated for 2 hours with test compounds, washed and cultured with different concentrations of Con A; and (2) lymphocytes are incubated for 24 hours with varied amounts of Con A, washed and then cultured with test compounds. The concentration of Con A used is either 0.04 or 0.05 μg/culture. The effects of some compounds of the invention are summarized as follows:

A. Sodium salt of α-(5-chlorobenzothiazol-2-ylthio)-benzene acetic acid. When the compound is cultured concomitantly with Con A present in the amounts of 0.02; 0.04; 0.06; and 0.08 μg/culture, the compound inhibits the Con A induced blastogenesis at concentrations of 0.1, 1.0, 5 and 10 μg/culture. When the compound is cultured with lymphocytes prior to addition of 0.04 or 0.05 μg/culture of Con A, the compound failed to show inhibitory activity. When the compound is cultured with lymphocytes 24 hours after the cells are incubated with 0.04 or 0.05 μg/culture of Con A, at concentrations of >2 or 3 μg/culture the compound showed strong inhibition of lymphocyte blastogenesis.

B. α-(5-Chlorobenzothiazol-2-ylthio)-α-(p-chlorophenyl)acetic acid. When this compound is cultured concomitantly with Con A present in the amounts of 0.02; 0.03; 0.04 and 0/06 μg/culture, the compound inhibits the Con A induced blastogenesis at concentrations >2 μg/culture. When the compound is cultured with lymphocytes prior to addition of 0.04 or 0.05 μg/culture of Con A, the compound shows consistent inhibitory activity at 3 and 5 μg/culture. When the compound is cultured with lymphocytes 24 hours after the cells are incubated with 0.04 or 0.05 μg/culture of Con A, at concentrations of >2 or 3 μg/culture the compound showed strong inhibition of blastogenesis.

These results clearly demonstrate that the compounds of the invention are strong and consistent inhibitors of T cell proliferation, which has been mitogenically induced. It is also clear that the compounds are able to perturb T lymphocyte blastogenesis when Con A binding sites are occupied, and so the compounds are not in competition with Con A for cell binding sites.

EXAMPLE 29

The ability of the compounds of the invention to modulate the immune response by influencing the growth and metastatic spread of murine Lewis lung carcinoma implanted subcutaneously, is evaluated.

The procedures employed for stock tumor maintenance and transfer, as well as for drug evaluation on the primary tumor, are those found in *Cancer Chemotherapy Reports*, Vol. 3, No. 2, September 1972, Protocol 1.400. The measurements of metastatic spread are made by counting tumor foci on the excised lung under an illuminated magnifying lens or a dissecting microscope, after employment of the Wexler india ink technique (Hilda Wexler, "Accurate Identification of Experimental Pulmonary Metastases", *J. Nat. Can. Inst.*, Volume 26, No. 4, April 1966, pp. 641–643) to accurately identify and count lung metastases.

According to the procedure, Lewis Lung (3H) tumor fragments are implanted by trochar implant subcutaneously into the axillary region of $BDF_1$ mice of 20 g. body weight. The animals are dosed intraperitoneally with the test compound indicated below in the quantity as specified. The animals are sacrified on the 13–14th day and the average number of metastatic foci and the mean weight of tumors in the group of treated animals relative to the mean tumor weight of the control animals, (T/C) for each group of animals is determined. When tested in this fashion, a ratio of average tumor weights of treated animals to average tumor weights of controls of less than or equal to 42% is considered to indicate that the compound tested exhibits activity in retarding the growth of the implanted tumor at that dose level.

The result of the assay is summarized as follows:

| Compound of Example No. | Dose[1] mg/kg | T/C | Average No. Metastases | % Reduction in Metastases |
|---|---|---|---|---|
| Example 21 | 50 | 85 | 18.8 | 28 |

-continued

| Compound of Example No. | Dose[1] mg/kg | T/C | Average No. Metastases | % Reduction in Metastases |
|---|---|---|---|---|
| Example 22 | 50 | 76 | 15.3 | 42 |
| Control | — | — | 26.2 | — |
| Example 24 | 50 | 112 | 28.7 | 31 |
| Control | — | — | 41.8 | — |

[1] Dose is administered intraperitoneally on day 1 only.

The results show that compounds of the invention have a significant effect in reducing the metastatic spread of Lewis Lung carcinoma, which is a reflection of the immunomodulatory activity of the compounds.

What is claimed is:

1. A compound having the formula:

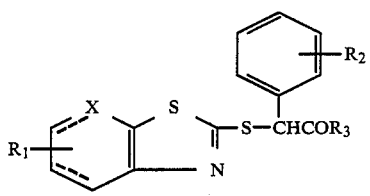

wherein $R_1$ is hydrogen, halo, nitro, amino, lower alkyl, lower alkoxy, trifluoromethyl or hydroxy; $R_2$ is hydrogen, fluorine, chlorine, bromine, lower alkyl, lower alkoxy amino, nitro, or trifluoromethyl; $R_3$ is hydroxy, lower alkoxy, amino, (lower)alkylamino, hydroxy(lower)alkyl amino, N-(lower)alkanoylamino(lower)alkoxy, N-arylcarbamoyl(lower)alkylthio, N,N-di(lower)alkylamino-N'-(lower)alkylamino, (lower)alkyl-N-(lower)alkanoylamino, cyano(lower)alkylamino, prolino, cysteino or piperidino(lower)alkylamino; X is CH or N, and where the dotted lines represent optional double bonds in the 5,6- and 7,8 positions, or a pharmacologically acceptable salt thereof.

2. The compound of claim 1, having the name α-(2-benzothiazolylthio)benzeneacetic acid.

3. The compound of claim 1, having the name α-(5-chlorobenzothiazol-2-ylthio)benzeneacetic acid.

4. The compound of claim 1, which is the sodium salt of α-(5-chlorobenzothiazol-2-ylthio)benzeneacetic acid.

5. The compound of claim 1, having the name α-(5-chlorobenzothiazol-2-ylthio)-α-(p-chlorophenyl)acetic acid.

6. The compound of claim 1, having the name α-(p-chlorophenyl)-α-(benzothiazol-2-ylthio)acetic acid.

7. The compound of claim 1, having the name α-(5-chloro-2-benzothiazolylthio)benzene acetic acid, ethyl ester.

8. The compound of claim 1, having the name α-(5-chlorobenzothiazol-2-ylthio)-α-phenylacetamide.

9. The compound of claim 1, having the name α-[(5-chloro-2-benzothiazolyl)thio]-N-(2-hydroxyethyl)benzeneacetamide.

10. The compound of claim 1, having the name α-[(5-chloro-2-benzothiazolyl)thio]benzene acetic acid, [2-(acetylamino)ethyl]ester.

11. The compound of claim 1, having the name α-[(5-chloro-2-benzothiazolyl)thio]benzeneethanethioic acid S-[2-(2-naphthalenylamino)-2-oxoethyl]ester.

12. The compound of claim 1, having the name α-[(5-chlorothiazolo[5,4-b]pyridin-2-yl)thio]-α-phenylacetic acid.

13. The compound of claim 1, having the name α-[(5-chlorothiazolo[5,4-b]pyridin-2-yl)thio]-α-(p-chlorophenyl)acetic acid.

14. The compound of claim 1, having the name α-phenyl-α-[(4,5,6,7-tetrahydrobenzothiazol-2-yl)thio]acetic acid.

15. The compound of claim 1, having the name α-[(6-nitro-2-benzothiazolyl)thio]benzeneacetic acid.

16. The compound of claim 1, having the name 4-chloro-α-[(5-chloro-2-benzothiazolyl)thio]benzeneacetamide.

17. The compound of claim 1, having the name α-[(5-chloro-2-benzothiazolyl)thio]-N-methylbenzeneacetamide.

18. The compound of claim 1, having the name α-[(5-chloro-2-benzothiazolyl)thio]-N-[2-(dimethylamino)ethyl]benzeneacetamide.

19. The compound of claim 1, having the name N-[[(5-chloro-2-benzothiazolyl)thio]phenylacetyl]glycine, ethyl ester.

20. The compound of claim 1, having the name α-[(5-chloro-2-benzothiazolyl)thio]-N-(cyanomethyl)benzeneacetamide.

21. The compound of claim 1, having the name 1-[[(2-benzothiazolyl)thio]phenylacetyl]-L-proline.

22. The compound of claim 1, having the name 1-[[(5-chloro-2-benzothiazolyl)thio]phenylacetyl)-L-proline.

23. The compound of claim 1, having the name α-[(5-chloro-2-benzothiazolyl)thio]-N-[2-(1-piperidinyl)ethyl]benzeneacetamide.

24. The compound of claim 1, having the name N-[[(5-chloro-2-benzothiazolyl]thio]phenylacetyl]-L-cysteine.

* * * * *